(12) United States Patent
Charriere et al.

(10) Patent No.: US 7,288,213 B1
(45) Date of Patent: Oct. 30, 2007

(54) METHOD FOR PREPARING LOW VISCOSITY TRICONDENSATE POLYFUNCTIONAL ISOCYANATES

(75) Inventors: Eugénie Charriere, Lyons (FR); Jean-Marie Bernard, Mornant (FR); Denis Revelant, Genas (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 09/673,951

(22) PCT Filed: Apr. 21, 1999

(86) PCT No.: PCT/FR99/00950

§ 371 (c)(1),
(2), (4) Date: Oct. 24, 2000

(87) PCT Pub. No.: WO99/55756

PCT Pub. Date: Nov. 4, 1999

(30) Foreign Application Priority Data

Apr. 24, 1998 (FR) .................................. 98 05170

(51) Int. Cl.
C07C 275/60 (2006.01)
C07C 275/62 (2006.01)
C07C 273/18 (2006.01)
C07D 251/34 (2006.01)
C07D 273/04 (2006.01)

(52) U.S. Cl. .............................. 252/182.2; 252/182.21; 252/182.22; 528/45; 528/49; 528/67; 528/73; 544/67; 544/222; 560/330; 560/335; 560/336; 560/355; 564/38; 564/44; 564/45

(58) Field of Classification Search ............. 252/182.2, 252/182.21, 182.22; 528/49, 67, 73, 45; 544/222, 67; 560/330, 335, 336, 355; 564/38, 564/44, 45
See application file for complete search history.

(56) References Cited

U.S. PATENT DOCUMENTS

| | | | | |
|---|---|---|---|---|
| 4,837,359 A | * | 6/1989 | Woynar et al. | 560/335 |
| 5,235,018 A | * | 8/1993 | Potter et al. | 528/49 |
| 5,258,482 A | | 11/1993 | Jacobs et al. | 528/49 |
| 5,914,383 A | * | 6/1999 | Richter et al. | 528/59 |

FOREIGN PATENT DOCUMENTS

| | | |
|---|---|---|
| EP | 0 277 353 | 8/1988 |
| EP | 0 649 866 | 4/1995 |

* cited by examiner

*Primary Examiner*—Rabon Sergent
(74) *Attorney, Agent, or Firm*—Buchanan, Ingersoll & Rooney, PC

(57) ABSTRACT

A method is described for preparing a tricondensate polyfunctional isocyanate composition, preferably having at least an isocyanurate and/or biuret group, which includes adding to a tricondensate polyfunctional isocyanate, or a mixture of different tricondensate polyfunctional isocyantes, obtained by (cyclo)condensation, in particular (cyclo)trimerization of one or several identical or different isocyanate monomers and optionally of another monomer, an allophanate of one or several identical or different isocyanates, or a mixture of different allophanates. The isocyanates or isocyanate monomer mixtures used for preparing the polyfunctional isocyanate(s) may be identical to or different from the isocyanate(s) or isocyanate mixture used for preparing the allophanate(s).

28 Claims, 1 Drawing Sheet

METHOD FOR PREPARING LOW VISCOSITY TRICONDENSATE POLYFUNCTIONAL ISOCYANATES

The invention relates to the preparation of reduced-viscosity polyisocyanate compositions which are intended in particular for two-component coating compositions, in particular paints.

Polyisocyanates are widely used in the coating industry, in particular in paints, on account of their many properties. In particular, it is known practice to use, as hardeners, polyisocyanates comprising isocyanurate groups on account of their crosslinking ability.

However, the compositions of this type obtained by trimerization of an isocyanate have a relatively high viscosity, making it necessary to use a substantial amount of solvent.

In point of fact, new regulations regarding environmental control demand a reduction in volatile organic compounds.

To satisfy these requirements, one of the possibilities consists in limiting the degree of conversion of the starting isocyanates, in particular of the diisocyanates, in order to minimize the formation of heavy compounds (polycondensates with a higher degree of polymerization, more particularly comprising more than one trimer unit) which are present in the trimerization medium and which are responsible for increasing the viscosity. To this end, the amount of catalyst is reduced for a fixed reaction time, or the duration of reaction is reduced for a given amount of catalyst, in order to increase the true cyclotrimer/heavy compound ratio.

The Applicant already markets products of this type, HDT (Hexamethylene Diisocyanate Trimer) and HDB (Hexamethylene Diisocyanate Biuret), which are referred to by the abbreviation LV meaning "Low Viscosity".

The drawbacks of these procedures are, in the first case, a large reduction in production efficiency and, in the second case, an increase in the cost due to the amount of catalyst used for a given amount of isocyanurates.

European patent applications EP 524 500 and EP 524 501 have also proposed carrying out an allophanatation reaction on a trimerization mixture or carrying out the trimerization in the presence of alcohols, which gives polyisocyanate mixtures containing isocyanurate functions, that are claimed as having a low viscosity.

Moreover, the fact that the viscosity of biuret compounds can be reduced by adding allophanates, or even by concomitant or consecutive allophanatation was not described.

The allophanates are obtained in the reaction medium by reacting a compound containing an alcohol function with an isocyanate, followed by reacting the carbamate function thus obtained with a new isocyanate molecule simultaneously or even consecutively with the trimerization reaction.

The processes for obtaining polyisocyanate compositions containing isocyanurate units having a significant content of allophanate functions have hitherto consisted in subjecting the trimerization mixture obtained after partial catalytic cyclotrimerization of the starting isocyanates to a consecutive allophanatation reaction in the presence of an alcohol, in particular butanol, followed by subsequent removal of the starting isocyanates by distillation under vacuum.

The compositions obtained according to the processes described in the patent applications mentioned above generally have a viscosity which is somewhat lower than that of compositions not comprising allophanates.

In the course of the study which led to the present invention, it has been shown, surprisingly, that it is possible to obtain a reduced viscosity for compositions with the same content of trifunctional (poly)isocyanates, in particular trimers (comprising at least one isocyanurate and/or biuret group). Thus, compared with isocyanurate (poly)isocyanate compositions comprising allophanates of the prior art, carrying out the catalytic (cyclo)trimerization reaction and the allophanatation reaction separately leads to a significantly reduced viscosity.

It has been demonstrated that the presence of polyfunctional isocyanate allophanates (having a functionality of at least three), in particular of allophanates containing isocyanurate groups in the final composition obtained according to the methods of the prior art, significantly and adversely increases the viscosity of this composition and that, in contrast, by working such that no polyfunctional isocyanate allophanates are formed, the viscosity of the final composition is significantly lower than the viscosity of the polyfunctional isocyanate composition obtained after trimerization of the starting isocyanates.

In the text hereinbelow the expression "comprising isocyanurate groups" will be used as a paradigm for polyfunctional compounds.

The aim of the invention is thus to provide polyfunctional isocyanate compositions comprising tricondensates preferably containing a biuret and/or isocyanurate function, the said composition comprising compounds containing allophanate functions and having a significantly reduced viscosity, preferably of at least about ¼, advantageously about ⅓, even more advantageously of about ⅖, in the absence of solvent, compared with the same composition comprising no compounds containing allophanate functions, for a given temperature.

In the present description, the term "about" means that the value given corresponds to a mathematical round-up and that any zeros furthest to the right are positional zeros rather than significant figures.

To this end, one subject of the invention is a process for preparing a tricondensate polyfunctional isocyanate composition, preferably comprising at least one isocyanurate and/or biuret group, which consists in adding to a tricondensate polyfunctional isocyanate, or to a mixture of different tricondensate polyfunctional isocyanates, obtained by (cyclo)condensation, in particular (cyclo)trimerization of one or more identical or different isocyanate monomers and optionally of another monomer, an allophanate of one or more identical or different isocyanates, or a mixture of different allophanates, the isocyanates or mixtures of isocyanate monomers used to prepare the polyfunctional isocyanate(s) being identical to or different from the isocyanate(s) or the mixture of isocyanates used to prepare the allophanate(s).

The (cyclo)tricondensate polyfunctional isocyanates of the invention correspond to the following general formula:

in which A represents an isocyanurate group of formula

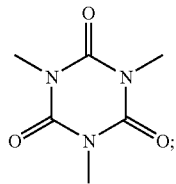

one of its derivatives containing an imino-oxadiazine-dione skeleton of the following general formula:

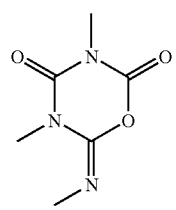

one of its derivatives containing an oxadiazine-trione skeleton of the following general formula

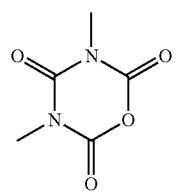

a biuret group of formula

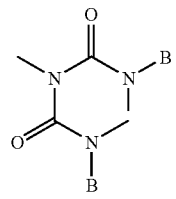

B being H or a hydrocarbon-based group, i.e. containing carbon and hydrogen as well as, optionally, other atoms (O, S, Si, etc.) preferably containing 1 to 20 carbon atoms; or a group of formula:

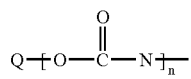

and in which $R_1$, $R_2$ and $R_3$, which may be identical or different, represent a hydrocarbon-based group, in particular an aliphatic, cycloaliphatic, heterocyclic or aromatic group, comprising a true or derived isocyanate function, Q is a hydrocarbon-based group, preferably alkyl, as defined for $R_1$ to $R_3$, m is an integer from 0 to 2, and n is the integer 3 or 4.

The expression "derived isocyanate function" means carbamate, urea, biuret, urethane, uretinedione, isocyanurate and masked isocyanate functions.

The tricondensate polyfunctional isocyanates can be homotricondensates (when $R_1$, $R_2$ and $R_3$ are identical) or heterotricondensates (when at least one from among $R_1$, $R_2$ and $R_3$ is different from the others).

The tricondensate polyfunctional isocyanate mixtures are defined as being a combination of different homotricondensate polyfunctional isocyanates, different heterotricondensate polyfunctional isocyanates or a mixture of the two categories.

The expression "true tricondensate polyfunctional isocyanate" will be used when $R_1$, $R_2$ and $R_3$, which may be identical or different, represent a group —A—X, A being a hydrocarbon-based chain as defined above, i.e. comprising at least carbon and hydrogen, and X being a hydrogen atom or an NCO group.

X preferably represents an NCO group.

In other words, the expression "true tricondensate polyfunctional isocyanate" means theoretical (cyclo)condensation products obtained by condensing three moles of monomers, advantageously of isocyanates, preferably diisocyanates or even triisocyanates (which may be identical or different), with the exception of compounds derived from the condensation of more than four monomers and/or comprising allophanate groups, as well as isocyanurate oligomers obtained by oligomerization of isocyanurate (poly) isocyanates.

The allophanates of the present invention correspond to the general formula II:

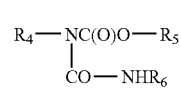

(II)

in which:

$R_4$ and $R_6$, which may be identical or different, represent a hydrocarbon-based group, in particular an aliphatic, cycloaliphatic, heterocyclic or aromatic group, as defined above, comprising a true or derived isocyanate function, $R_5$ representing an alkyl group, i.e. the residue of an alcohol compound after removal of the OH function.

In this case, the expression "derived isocyanate function" means carbamate, urea, biuret, urethane, uretinedione, masked isocyanate and allophanate functions, with the exclusion of the isocyanurate function.

When $R_4$ is identical to $R_6$, the term "homo-allophanates" will be used, these being obtained by condensing, onto a carbamate formed by reaction of an isocyanate of formula $R_4NCO$ with an alcohol of formula $R_5OH$, a second isocyanate of formula $R_6NCO$, $R_6$ being identical to $R_4$.

The allophanates can also be obtained by condensing, onto the carbamate, a second isocyanate $R_6NCO$, $R_6$ being different from $R_4$, in which case the term "hetero-allophanates" will be used.

Advantageously, a mixture of allophanates comprising at least ¼, advantageously at least ⅓ and preferably at least ⅔ (by mass) of primary allophanate(s), advantageously of a monoalcohol, is added.

The mixture can also comprise bis-allophanates, tris-allophanates and heavy allophanates, as well as smaller proportions of the carbamate of the isocyanate(s) ($R_4NCO$ and/or $R_6NCO$) and of alcohol ($R_5OH$).

It is very desirable that the mixture should comprise at least ½ (by mass), advantageously not more than ⅓, preferably ⅙, of heavy allophanates (comprising more than two allophanate functions).

It should be pointed out that the bis-allophanates and tris-allophanates, in particular the bis-allophanates and tris-allophanates of monoalcohols, when added to tricondensate polyfunctional polyisocyanates as thinners, are not generally a cause of a significant increase in viscosity, unlike heavy allophanates.

The bis-allophanates and tris-allophanates even contribute towards the thinning properties of the mono-allophanate.

In the context of the invention, an allophanate composition comprising solely bis-allophanates and tris-allophanates can be added to the tricondensate polyfunctional isocyanate composition.

However, this embodiment is not preferred on account of the difficulty in preparing a composition free of mono-allophanate.

Thus, in the case of a monofunctional alcohol in particular, the sum of the mono-, bis- and tris-allophanates added as thinners to the tricondensate polyfunctional isocyanate composition is advantageously at least ⅔ and preferably at least 75%, preferably at least 90%, by weight relative to the total weight of the allophanate composition after removal of the unreacted monomers.

The amount of bis-allophanates can be up to 10% or even 20% by weight relative to the total weight of the allophanate composition without substantially modifying the thinning properties of this composition.

In parallel, the amount of tris-allophanates can represent up to 30% by weight relative to the total weight of the allophanate composition. However, this amount preferably does not exceed 20%, and preferentially 15%, by weight.

The allophanate composition added to the tricondensate polyfunctional isocyanate composition still has very good thinning properties when the ratio $$\frac{\text{bis-allophanate functions} + \text{tris-allophanate functions}}{\text{mono-allophanate functions}} \text{ is greater than or equal to } 0.1,$$

and can be up to 0.3 or even 0.5.

Given that the (poly)isocyanate composition to be thinned contains only a small amount of allophanates, the above characteristics are found in the ratios between allophanates of the final mixture.

Depending on the viscosity of the composition to be thinned, an allophanate composition should be used whose viscosity at 25° C. is not more than 45%, advantageously 35%, preferably 30%, of the viscosity of the (poly)isocyanate composition to be thinned.

The term "primary" allophanate means the theoretical molecular reaction product expected from the reaction between the isocyanate(s) and the alcohol corresponding to the product of reaction of two moles of isocyanate function per mole of alcohol function.

In the case of diols, the primary allophanate is the product of reaction of four moles of isocyanates with one mole of diol. This is thus a di-allophanate which must be distinguished from bis-allophanates and higher homologues, which are the products of oligomerization of primary allophanates.

The primary allophanate is obtained from a single alcohol molecule: bearing one or more hydroxyl functions converted into allophanate functions.

Thus, the allophanate is true when the following condition is met:

$$\frac{\begin{array}{c}\text{Total number of allophanate functions per molecule}\\ \text{of compound bearing allophanate functions}\end{array}}{\begin{array}{c}\text{Number of identical or different isocyanate chains}\\ \text{engaged in the allophanate functions borne by the}\\ \text{compound molecule which bear allophanate functions}\end{array}} = 1/2.$$

The term "mono-allophanate" means the theoretical reaction product from reacting one mole of isocyanate $R_4NCO$ with one mole of alcohol ($R_5OH$) and of one mole of isocyanate $R_6NCO$ with the carbamate function thus formed.

A bis-allophanate is a molecule which is characterized by the fact that it comprises two allophanate functions, separated by an at least partially hydrocarbon-based chain.

In the case of these molecules, the ratio indicated above is greater than ½, the calculation of this ratio not taking into account the allophanate molecules containing carbamate functions.

When the starting isocyanates are diisocyanates, the bis-allophanates are obtained either from monoalcohols or from diols.

In the case of monoalcohols, the bis-allophanate molecule comprises 3 isocyanate monomers and 2 alcohol molecules. In the case of diols, the bis-allophanate molecule comprises 4 isocyanate molecules.

The bis-allophanates obtained from a diol are less thinning than those obtained from the double attack of a monoalcohol, but can raise the content of isocyanate functions and provide a greater crosslinking effect.

The tris-allophanates are defined in the same way as the bis-allophanates.

When the allophanates are synthesized from several alcohols comprising diols, it is preferable to start by synthesizing the bis-allophanates obtained from diols in order to avoid their polycondensation.

In addition, according to the invention, a combination of different homoallophanates, of different heteroallophanates or a mixture of these two categories, or alternatively a mixture of homoallophanates and/or of heteroallophanates obtained with different alcohols, can also be added to the tricondensate polyfunctional isocyanates.

The term "heavy" condensate compounds means those obtained by reacting more than four monomers with one another.

The term "heavy allophanates" means the allophanate products which do not fall into any of the categories previously defined.

In particular, allophanates comprising a derived isocyanate function (biuret and/or isocyanurate) and at least one allophanate function and compounds comprising at least three allophanate functions, which are also known as tri-condensate allophanates, fall within the category of heavy allophanates.

The present invention is not limited to the nature of the isocyanate monomers used. Thus, the isocyanate monomers can be aliphatic, including cycloaliphatic and arylaliphatic, mono- advantageously di- or triisocyanates, preferably diisocyanates, such as:

polymethylene diisocyanates and in particular hexamethylene diisocyanate, 2-methyl pentamethylene diisocyanate, 4-isocyanatomethyl octamethylene diisocyanate or 2,4,4-trimethyl hexamethylene diisocyanate;

isophorone diisocyanate, norbornane diisocyanate, 1,3-bis(isocyanatbmethyl)cyclohexane (BIC), $H_{12}$-MDI and cyclohexyl 1,4-diisocyanate;

arylenedialkylene diisocyanates (such as OCN—$(CH_2)_p$-Ø-$(CH_2)_q$—NCO) p and q being identical or different integers between 1 and 6, preferably 2 and 4;

or alternatively aromatic isocyanates such as tolylene diisocyanate.

The aromatic isocyanates and the isocyanates whose isocyanate function is borne by a neopentyl carbon are not preferred.

The preferred isocyanates targeted by the invention are those in which at least one, advantageously two, preferably three, of the following conditions are met:

at least one, advantageously two, of the NCO functions are linked to a hydrocarbon-based skeleton via a saturated ($sp^3$) carbon;

at least one, advantageously two, of the said saturated ($sp^3$) carbons bears at least one, advantageously two, hydrogen(s). In other words, it has been found that better results are obtained when the carbon bearing the isocyanate function bears a hydrogen, preferably two hydrogens. It is also even preferable for at least a third, advantageously at least a half, preferably at least two thirds, of the said saturated ($sp^3$) carbons to be linked to the said skeleton via a carbon atom which itself bears at least one hydrogen, more preferably two;

all the intermediate carbons via which the isocyanate functions are linked to the hydrocarbon-based skeleton are saturated ($sp^3$) carbons which advantageously partially, preferably totally, bear a hydrogen, preferably two hydrogens. It is also even preferable that at least a third, advantageously at least a half, preferably at least two thirds, of the said saturated ($sp^3$) carbons are linked to the said skeleton via a carbon atom which itself bears at least one hydrogen, more preferably two.

In general, the preferred starting isocyanates (monomers) are those comprising at least one polymethylene chain (comprising from 2 to 6 methylene chain units).

The preferred isocyanates, in particular aliphatic diisocyanates, especially $C_1$-$C_{10}$ alkyl isocyanates, are those in which the alkyl chain is linear or weakly branched. The expression "weak branching" means the absence of tertiary and neopentyl carbons.

HDI, IPDI, NBDI, $H_{12}$-MDI and MPDI are particularly preferred.

In general, since aliphatic isocyanates generally speaking have a lower viscosity than cycloaliphatic isocyanates, it will be preferred to avoid the use of isocyanate allophanates containing cycloaliphatic functions when the desired effect is to reduce the viscosity of the isocyanurate (poly)isocyanates obtained from isocyanates containing aliphatic functions.

In general, in order to obtain a relatively significant reduction in the level of viscosity, the mixture needs to be such that it has a viscosity which is lower than that of the initial mixture, free of monomers and solvents, i.e. by at least about ¼, preferably by at least about ⅓ and advantageously by at least about ⅔, compared with that of the initial mixture without allophanates.

A subject of the invention is, more particularly, a process for preparing a reduced-viscosity tricondensate polyfunctional isocyanate composition from isocyanates, comprising the following steps a) and b) in any order:

a)(cyclo)condensation, in the presence of a catalyst, of one or more identical or different first isocyanate monomer(s) until the desired degree of conversion is obtained;

b) reaction of one or more second isocyanate monomer(s) which are identical to or different from one another and identical to or different from the first isocyanate monomer(s), with an alcohol to form a carbamate, the reaction optionally being catalyzed, and simultaneous or subsequent reaction of the carbamate with one or more isocyanate monomer(s) which are identical to or different from the previous monomers, to give an allophanate or mixture of allophanates;

and steps c) and d) in any order:

c) mixing the reaction product from step a) with all or some of the reaction product from step b); and optionally d) removing the isocyanate monomers.

The (cyclo)condensation reaction is advantageously a (cyclo)trimerization reaction, which is carried out in the presence of a (cyclo)trimerization catalyst that is known per se.

When a catalyst is used for the carbamatation reaction, the same catalyst will advantageously be used for the allophanatation reaction. However, different catalysts may be used.

The carbamatation and allophanatation reactions can be carried out in two stages, for example by increasing the temperature of the reaction medium until the carbamatation reaction takes place, and subsequently increasing the temperature until the allophanatation reaction takes place.

The two reactions can also take place simultaneously by increasing the reaction temperature directly up to the allophanatation temperature.

It is possible to use in steps a) and b) of the process the same isocyanate monomer(s) which will then be subjected in parallel to a catalytic trimerization and a carbamatation reaction followed by an allophanatation reaction, the optionally purified reaction media then being mixed until the desired viscosity is obtained.

In order to reduce the viscosity of a tricondensate polyfunctional isocyanate of a higher alkyl (containing more than 10 carbon atoms) which is optionally branched, cycloalkyl or aromatic and which thus has a higher viscosity than that of a lower alkyl polyisocyanate (containing not more than 10 carbon atoms), it is also possible to add to the trimerization product the product obtained after carbamatation and allophanatation of one or more isocyanate(s) different from the first isocyanate(s) and having a lower viscosity than that which would be obtained by carbamatation and then allophanatation of the first isocyanate(s).

To this end, the isocyanate(s) used for the carbamatation/allophanatation reactions will advantageously be one or more linear alkyl isocyanate(s), in particular HDI.

Step a) is carried out under the usual conditions for the catalytic trimerization of isocyanates.

Mention may be made, by way of example, in the case of the tricondensates containing isocyanate functions, of the conventional reaction of HDI by catalysis in the presence of an aminosilyl derivative, in particular a silane or a disilazane, preferably hexamethyldisilazane (HMDZ) as described in EP 57 653 or in the presence of a quaternary ammonium catalyst.

The reaction conditions comprise, in particular for a reaction catalyzed with HMDZ, an amount of catalyst of the order of 1.2% by weight relative to the weight of the HDI, a reaction time of about 2 h 30 minutes and a temperature of about 120° C.

Under these conditions, the degree of conversion of the isocyanate functions is 32.7%, which corresponds to the production of an isocyanurate (poly)isocyanate mixture whose content of true HDI trimer functions (comprising a single isocyanurate ring) is about 50% by weight.

Mention may also be made of reactions catalyzed with carboxylic acids in the presence of water in order to obtain condensates containing biuret units (patent FR 86/12524).

Step b) comprises a conventional carbamatation reaction followed by a conventional allophanatation reaction, the two reactions possibly being catalyzed with the same catalyst or a combination of catalysts, and the two reactions possibly proceeding simultaneously in a single reactor.

In a first stage, the isocyanate(s) used for the allophanatation reaction, which may be identical to or different from the isocyanate(s) used for the (cyclo)condensation reaction, advantageously the (cyclo)trimerization reaction, is (are) optionally reacted in the presence of an allophanatation catalyst with one or more compounds comprising at least one alcohol function. The reaction is carried out at a temperature which is advantageously from about 80° C. to about 100° C., when the carbamatation and allophanatation reactions are carried out in two stages, or directly at a temperature of about 100° C. to 180° C. when the carbamatation and allophanatation reactions are carried out simultaneously.

An alcohol containing an aliphatic chain, including alcohols containing a cycloaliphatic chain or, preferably, an alcohol containing a linear or weakly branched alkyl chain, comprising only one OH function is advantageously used. Mention may be made in particular of alkyl alcohols containing a linear $C_1$-$C_{10}$ chain, $C_4$-$C_8$ alcohols being preferred.

The weakly branched aliphatic alcohols are, in particular, $C_3$-$C_{20}$ aliphatic alcohols comprising at least one and preferably not more than four secondary carbon atoms. Mention may be made in particular of primary alcohols containing an ethylhexyl chain, in particular a 2-ethylhexyl chain.

Suitable alcohols can also optionally comprise one or more double bonds.

The compound comprising at least one alcohol function can also comprise one or more other functions, such as cetone, nitrile, ester, ether or polyether (in particular polyethylene oxide monoether advantageously comprising not more than 20 and preferably not more than 10 polyethylene oxide chain units), siloxane (U.S. Pat. No. 6,536,556) or fluoro (JP 81-49329).

Diols, in particular $C_2$-$C_{40}$ diols containing a linear or branched alkyl chain as defined above for the monoalcohols, can also be used. However, these generally give products of substantially higher viscosity than their monohydroxylated homologues and are generally used as a mixture with monoalcohols only when a crosslinking effect rather than a chain-extending effect is desired.

The alcohol compound can be a polyester or acrylic oligomer such as, for example, the commercial derivatives K Flex 188 or oligomers derived from castor oil such as the commercial products CASPOL 1842, 5001, 5003, 5007, 5002, etc.

Other alcohols that are particularly advantageous from the point of view of low viscosity are monoalcohol esters and/or ethers, in particular the compounds of formula R—[O—CH(R$_1$)—CH$_2$]$_n$—OH, in which R$_1$ represents H or an alkyl group, preferably a $C_1$-$C_8$ alkyl group, in particular methyl, or polyether, in particular —CH$_2$OR$_{10}$, R$_{10}$ representing a hydrocarbon-based chain as defined above, in particular polyoxyalkylene, preferably polyoxyethylene, n is an integer preferably from 1 to 50, and R is a linear or branched $C_1$-$C_{20}$ alkyl group, or R is a group

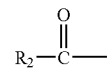

with $R_2$ being a linear or branched $C_1$-$C_{20}$ alkyl group.

As mentioned above, the aliphatic chain of the compound comprising at least one OH function can also be substituted or interrupted with a cycloalkyl or heterocyclic group.

The OH function can be linked directly to a carbon atom of a hydrocarbon-based ring or of the heterocycle.

Silanol-type derivatives are also suitable.

The reaction is generally continued until an NCO content corresponding to the consumption of at least 80% of the alcohol functions is obtained.

A mixture of compounds containing different alcohol function(s) can also be added during the carbamatation/allophanatation reaction.

When the actual carbamatation and allophanatation reactions are dissociated, it is possible, after carbamatation, in a second stage, to raise the temperature of the reaction medium up to about 100° C.-180° C., preferably in the region of 140° C. for HDI, in order to carry out the allophanatation reaction, this reaction optionally being carried out in the presence of an allophanatation catalyst, in particular a catalyst based on tin, zinc or other metals known to those skilled in the art. Mention may be made in particular of dibutyltin dilaurate (DBTL), tin bis(2-ethyl hexanoate) and tin dichloride, DBTL being preferred.

The amounts of catalyst are advantageously between 0.001% and 0.1%, in particularly 0.001% and 0.05%, preferably about 0.005% by weight of metal relative to the weight of isocyanate(s).

The reaction time is advantageously from about 1 to 24 hours, preferably between 3 and 7 hours.

The allophanatation reaction is carried out so as to predominantly obtain primary allophanates, as defined above.

An isocyanate different from the one used in the carbamatation reaction can be used. In this case, a mixed allophanate is obtained.

In order to predominantly obtain primary allophanates, the isocyanate (NCO) functions/hydroxyl (OH) functions ratio is advantageously high. A ratio of greater than 4 and better still greater than 6 will preferably be used, a ratio of about 8 being particularly advantageous.

In the case of difunctional or polyfunctional alcohols, an (NCO)/OH ratio of greater than 10 is more advantageous.

When the NCO/OH ratio is low, the viscosity of the final product is high on account of the significantly higher presence of heavy allophanates such as the bis-allophanate oligomers or higher homologues. Thus, the viscosity of the HDI butyl allophanate is multiplied by 4 when the NCO/OH ratio is reduced from 8 to 4.

The reactions of step a) and of step b) are monitored by measuring the NCO titres.

Step c) is carried out by mixing the products from steps a) and b) in proportions varying as a function of the desired final viscosity, in accordance with the empirical law given by the formula:

Log $\eta_{mixture}$=Sum$x_i$ Log $\eta_i$ with $\eta$ being the viscosity of the product or of the mixture and x being the mass fraction of the products in the mixture.

This law makes it possible to evaluate the amount of allophanate(s) which should be added to a polyisocyanate composition to be thinned as a function of the viscosity which it is desired to obtain.

In the course of the present invention, it has been demonstrated, surprisingly, that, although the compositions to be mixed together are of different structure and different molecular mass, they satisfy this law qualitatively or semi-quantitatively.

In general, the organometallic catalyst(s) is (are) found in the final allophanate. The isocyanate monomers are separated from the converted compounds by distillation or by any other separation process (crystallization, extraction with gases in the critical or supercritical state, etc.) which can be carried out separately at the end of reactions a) and b) on the tricondensate polyfunctional isocyanate or the mixture of tricondensate polyfunctional isocyanates, on the one hand, and on the primary allophanate or the mixture of allophanates in the corresponding reactors or after the tricondensate polyfunctional isocyanate(s) and allophanate(s) have been mixed together, i.e. on the allophanate/tricondensate polyfunctional isocyanate mixture.

For the purpose of teaching by example (paradigm), in order to obtain compositions comprising an HDI trimer containing an isocyanurate unit (HDT), a viscosity of 700 mPa·s can be obtained by adding to a trimerization product HDI obtained by trimerization with a limited degree of conversion of the HDI of about 20%, having a viscosity of about 1200 mpa·s at 25° C., an amount of the allophanatation product such that the amount of primary HDI butyl allophanate in the final product is greater than or equal to about 3 per 100 g of final mixture, i.e. to about 15% by weight of primary allophanate per 100 g of final mixture.

Thus, when HDT having a viscosity of 2700 mpa·s at 25° C. is used, the viscosity can be reduced to 1200 mPa·s at 25° C. by adding an amount of allophanates of about 25% by weight relative to the weight of the final mixture in order to obtain a final concentration of about 15% by weight of primary allophanate.

Step d) is advantageously carried out by vacuum distillation of the HDI under the usual conditions.

The compositions obtained according to the invention contain the true tricondensate polyfunctional isocyanate(s) as well as heavy condensates, obtained by catalytic (cyclo) condensation of the starting isocyanate monomer(s) (first isocyanate(s) and optionally other monomers present), the primary monoallophanate and the heavy allophanate compounds such as di- and tri-allophanates, the second isocyanate(s) and optionally third isocyanate(s) (in the case of heteroallophanates) and the alcohol or the mixture of alcohols used for the carbamatation reaction, bis-allophanate, tris-allophanate and higher homologues. The allophanatation reaction is carried out such that the residual amount of carbamates (intermediate product not entirely converted) is small (generally less than 20%, advantageously less than 10% and preferably less than 5%, by weight).

In general, the ratio:

$$\frac{\text{Carbamate functions obtained from the alcohol molecule(s) used to make the allophanate}}{\text{Allophanate functions obtained from the alcohol molecule(s) used to make the allophanate}}$$

is less than 0.5, preferably less than 0.2 and advantageously less than 0.1.

The process according to the present invention is particularly suitable for tricondensates comprising biuret units which generally generate high viscosities. However, when isocyanurate-based tricondensates are used, the amount of components comprising biuret units is preferably not high (less than 50%, preferably less than 25% and advantageously less than 10%).

However, even when the content of biuret units is between 0.5 and 5% by mass of the isocyanurate units, excellent results are still obtained.

In the absence of biuret units and especially when mixtures termed "low-viscosity", i.e. mixtures having a viscosity of not more than 1500 mPa·s, generally 1300 mpa·s, at 25° C., are used as starting isocyanurates, it is preferable, in order to obtain a significant reduction by adding a small proportion of allophanates (not more than about 30% by mass), to take allophanate mixtures whose viscosity is less than 500 mPa·s, preferably less than 200 mPa·s.

The composition according to the invention contains virtually no allophanates comprising tricondensate units, in particular isocyanurate obtained by cyclotrimerization of the starting isocyanate. Advantageously, it comprises less than 10%, advantageously less than 8%, even more advantageously less than 5%, preferably less than 4% and more preferably less than 3%, and even more preferably less than 2%, it being possible for it to be as low as 1%, by weight, relative to the total weight of the composition.

In general, the compositions are characterized by an amount of allophanate compounds which is generally greater than 5% by weight and by a high G ratio defined below:

$$G = \frac{\text{True tricondensate polyisocyanates, obtained from the condensation of three identical or different isocyanate molecules not modified with carbamate or allophanate}}{\text{Sum of the polyisocyanate molecules bearing at least one tricondensate function obtained from the condensation of three identical or different isocyanate molecules}}.$$

(The assembly of molecules bearing at least one tricondensate function is formed by the true tricondensate polyisocyanate compounds, the tricondensate polisocyanate compounds in which at least one isocyanate function is engaged in a carbamate function, or an allophanate function or a heterocyclic function chosen from uretidine dione, isocyanurate, etc. functions).

The G ratio is generally greater than 0.3, preferably greater than 0.4 and advantageously greater than 0.5.

Such a composition is novel.

A subject of the invention is thus also a reduced-viscosity tricondensate polyfunctional isocyanate composition comprising at least one true tricondensate polyfunctional isocyanate and at least one primary allophanate, the said composition being characterized in that it comprises less than 10%, advantageously less than 8%, even more advantageously less than 5%, preferably less than 4% and more preferably less than 3%, and even more preferably less than 2%, it being possible for it to be less than 1% of tricondensate allophanates relative to the total weight of the composition.

A subject of the invention is also a tricondensate polyfunctional isocyanate composition of significantly reduced viscosity, comprising at least one true tricondensate polyfunctional isocyanate and at least one primary allophanate, the said composition satisfying at least one of the following conditions:

a G ratio generally greater than 0.3, preferably greater than 0.4 and advantageously greater than 0.5, a primary allophanate/primary allophanate+true trimer weight ratio of between 2.5% and 99%, advantageously between 3% and 60% and preferably between 3.5% and 40%, the tricondensates are obtained from a tricondensation reaction for which the degree of conversion of the identical or different isocyanate monomer(s) into tricondensate polyfunctional polyisocyanates contained in the composition is greater than 8%, preferably greater than 10% and advantageously greater than 15%, at least 1% and not more than 99%, preferably at least 2% and not more than 75%, of biuret is present, these amounts being given on a weight basis.

Advantageously, it is preferable for the low-viscosity tricondensate polyfunctional isocyanate compositions comprising at least one true tricondensate polyfunctional isocyanate and at least one allophanate to satisfy the first two conditions, or even the first three conditions and better still the four conditions above.

In order to obtain low-viscosity compositions comprising tricondensate polyfunctional isocyanates from cycloaliphatic isocyanates, the process can be carried out in the same way as described above and a small amount of solvent (generally less than ⅓, advantageously less than ¼ and preferably less than ¹⁄₁₀ by weight, relative to the total weight of the composition) can optionally be added.

The compositions obtained according to the invention can be in the form of powders and can give a reduced viscosity on changing to the molten state, compared with products containing no primary allophanates.

The compositions in their various formulations, as aqueous or aqueous-organic solutions or in the form of powders, can also comprise identical or different protecting groups for the isocyanate functions. The isocyanate functions can be partially or totally protected. The ratio of free isocyanate functions to masked isocyanate functions is chosen by a person skilled in the art as a function of the intended application.

The compositions obtained according to the invent-ion can be used as aqueous formulations optionally with addition of formulation additives such as ionic or nonionic surfactants, or reversible or irreversible grafting onto the isocyanate functions of various polyoxyalkylene compounds such as polyethylene glycol derivatives or polyoxyethylenated amines.

These polyisocyanate compositions, containing isocyanate functions that are optionally partially or totally masked, can also give emulsions or suspensions as described in FR 2 703 357 and EP 691 993.

Polyols can also serve as formulating agents for these polyisocyanate compositions, to make aqueous solutions, emulsions or dispersions.

Similarly, these compositions can be used to prepare polyurethane compositions in powder or dissolved form or in aqueous or aqueous-organic solution, optionally masked with temporary and/or permanent masking agents. The choice of the polyol then depends on the intended application.

The compositions which are the subject of the present invention are used with conventional coating additives, i.e. wetting agents, pigments, spreading agents, mar-resistance agents and any other compound known to those skilled in the art used in the applications mentioned above.

Among the many advantages offered by the invention, besides the reduced viscosity, mention may be made of the fact that the process according to the invention makes it possible to control the viscosity quickly and easily by adjusting the amount of one or other of the components (tricondensate polyfunctional isocyanates or allophanate(s)) of the mixture without being obliged to carry out a total synthesis, from the starting monomers and the alcohol.

In addition, for the same yield of allophanates relative to the process of the prior art, the degree of conversion of the monomer for a given viscosity is significantly higher.

The examples which follow illustrate the invention.

The NCO titre is expressed either as a % of NCO per 100 g of mixture or as moles of NCO per 100 g of mixture.

EXAMPLE 1

Preparation of Low-Viscosity (LV) HDT 4584 g of hexamethylene diisocyanate (HDI) were introduced into a 6 liter three-necked reactor. The reaction medium is heated and stirred. 27.5 g of hexamethyl disilazane (HMDZ) are added at 113° C. The temperature of the reaction medium is then raised to 120° C. The temperature is maintained for 2 hours 15 minutes. The NCO titre measured at this stage is 1.069 mol of NCO per 100 g of mixture, which gives a degree of conversion of the HDI of 19.3%. The temperature of the reaction medium is reduced to 80° C. and 16 ml of n-butanol are added to quench the trimerization reaction. After reaction for one hour, the HDI monomer is removed by evaporation under vacuum to give an HDT product which has a viscosity of 1260 mPa·s at 25° C., a residual HDI content of less than 0.15% and a coloration of 5 hazen.

EXAMPLE 2

Preparation of a Very Low-Viscosity HDI Butyl Allophanate 4830 g of HDI are introduced into a 6-1 reactor. 532 g of n-butanol are added over 50 minutes with stirring, while allowing the reaction temperature to rise to 108° C. 1.3 g of dibutyltin dilaurate are added at 125° C. and the temperature is raised to 140° C. After reaction for 5 hours at about 140° C., the reaction is stopped by cooling. The NCO titre is 0.786 mol of NCO per 100 g of mixture. The HDI monomer is removed by evaporation under vacuum to give an HDI n-butyl allophanate with a viscosity equal to 140 cps and a titre of 0.405 mol of NCO per 100 g of product, i.e. 17% by weight of NCO per 100 g of mixture. The recovered yield of finished product is about 50% by weight. The amount of residual HDI is 0.05%. The amount of true primary HDI n-butyl allophanates is 57.8% by weight. The colour of the product is 10-15 hazen.

EXAMPLE 3

Medium-Viscosity HDI Butyl Allophanate

The process is performed in the same way as in Example 2, but with an NCO/OH ratio of 4.

The product has a viscosity of 600 mPa·s at 25° C., an NCO titre of 0.303, i.e. 12.7%, and an titre of residual HDI monomer of 0.1%. The recovered yield of finished product is 76.6% by weight. The composition of the product obtained is as follows, on a weight basis:

| | |
|---|---|
| primary HDI n-butyl allophanate (mono-allophanate) | 30.6% |
| butyl monocarbamate | 1% |
| bis-allophanate | 25.7% |
| tris-allophanate | 18.0% |
| heavy isocyanates | 24.7%. |

The colour of the product is 10-15 hazen.

EXAMPLE 4

Preparation of the Low-Viscosity Mixture

The mixture was prepared by applying the viscosity law given above.

A mixture containing 75% by weight of the composition obtained in Example 1 with 25% by weight of the composition obtained in Example 2 was prepared.

The characteristics of the products are obtained from analyses, quantified by infrared, of products separated on a separating column.

The characteristics of the mixture are given in the table below.

TABLE

Characteristics of an HDI butyl allophanate HDT mixture.

| | Product of Example 1 | Product of Example 2 | Characteristics of the mixtures | |
|---|---|---|---|---|
| % of primary HDI n-butyl allophanate | 0.7% | 56.8% | 14.45 | 14.45 |
| % true (cyclo)tri-condensate | 61% | 0% | 45.75 | 45 |
| G ratio true (cyclo)tri-condensate/sum of the (cyclo)tri-condensates | 0.69 | 0 | 0.69 | 0.68 |
| Primary allophanate/ primary allophanate + true (cyclo)tri-condensate | 1% | | 24% | 23.8% |
| Biuret functions | 6% | | 4.5% | 4.5% |
| Viscosity (mPa · s at 25° C.) (falling ball test) | 1260 | 600 | 720 | 730 |

The increase in viscosity expressed by the ratio: (viscosity of the product of Example 1—viscosity of the mixture)/viscosity of the product of Example 1 is equal to 42.9%.

EXAMPLE 5

Viscosities of Mixtures According to the Invention as a Function of the Allophanate Content HDT obtained according to Example 1 was mixed in variable proportions with allophanates obtained according to Example 2.

BRIEF DESCRIPTION OF THE DRAWING

The viscosities are given in the attached FIGURE.

EXAMPLE 6

Viscosities of HDB/HDI Butyl Allophanate Mixtures

Figure 1:
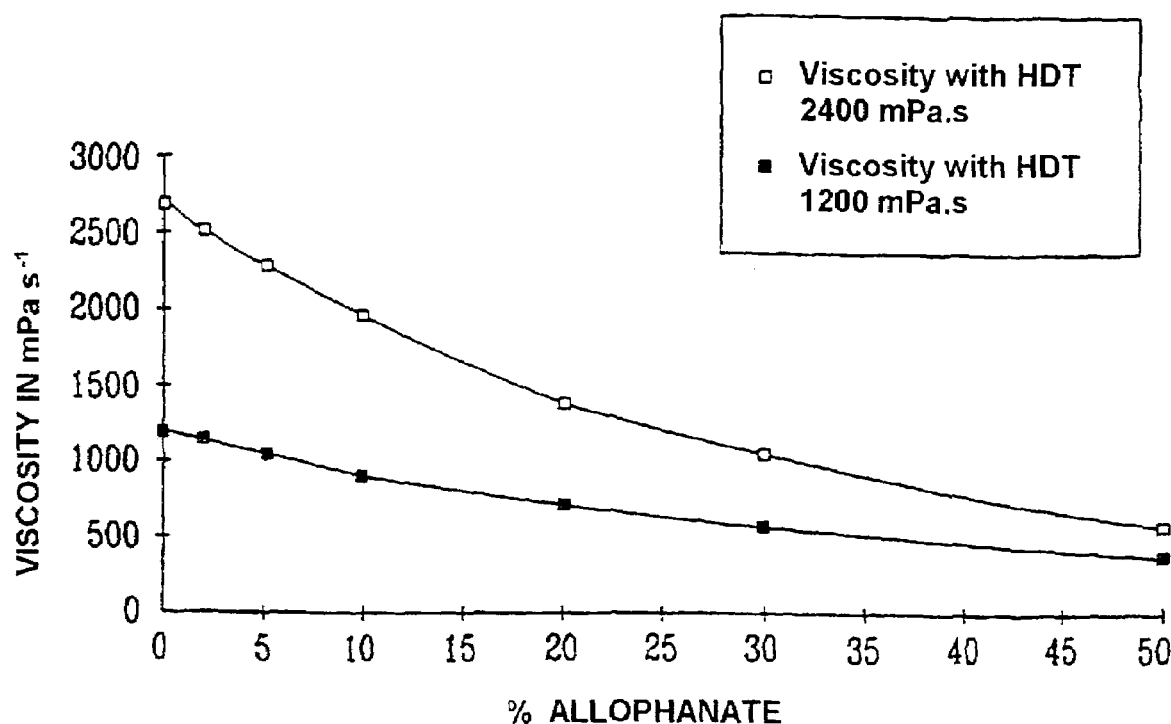

Hexamethylene diisocyanate biuret (HDB)/HDI butyl allophanate mixtures were prepared as described above in variable proportions and their viscosity measured.

The results are given in the table below:

TABLE

Characteristics of an HDB/HDI butyl allophanate mixture.

| HDB (% by weight) | HDI butyl allophanate (% by weight) | Viscosity (mPa · s at 25° C.) | |
|---|---|---|---|
| | | (1) | (2) |
| 100 | 0 | 10500 | 17100 |
| 90 | 10 | 6200 | 10250 |
| 75 | 25 | 3300 | 4600 |
| 50 | 50 | 750 | 1450 |

(1) HDB of standard viscosity (DC monomers ≈ 40%)
(2) HDB of high viscosity

EXAMPLE 7

Synthesis of a Low-Viscosity Norbornane Diisocyanate Trimer (LV NBDT)

The product is synthesized according to the same protocol as that described for Example 1, using 0.75 g of hexamethyl disilazane per 100 g of norbornane diisocyanate (NBDI) and a reaction time of 3 hours at 120° C. The degree of conversion of the NBDI before the reaction is stopped is 20%.

The product purified of the excess monomer by distillation is a solid which has a measured viscosity of 4070 mPa·s at 25° C. and at 80% solids content in n-butyl acetate and of 252 mPa·s at 25° C. and at 70% solid content in n-butyl acetate.

EXAMPLE 8

Synthesis of a Norbornane Diisocyanate Trimer (NBDT)

The product is synthesized according to the same protocol as that described for Example 1, using 1.4 g of hexamethyl disilazane per 100 g of norbornane diisocyanate (NBDI) and a reaction time of 3 hours at 120° C. The degree of conversion of the NBDI before the reaction is stopped is 26.4%. The product purified of the excess monomer by distillation is a solid which has a measured viscosity of 13400 mpa·s at 25° C. and at 80% solids content in n-butyl acetate.

EXAMPLE 9

Preparation of NBDT/Low-Viscosity HDI N-Butyl Allophanate Compositions

The compositions were prepared as indicated in the following table:

| | Product of Example 8 | Product of Example 9 | Product of Example 2 | Characteristics of the mixtures | |
|---|---|---|---|---|---|
| % of composition by weight | | | | 60/40 Example 2/ Example 8 | 60/40 Example 2/ Example 9 |
| DC of HDI | | | 50% | | |
| DC of NBDI | 20% | 26.4% | | | |
| Residual HDI | | | 0.05 | 0.03 | 0.03 |
| Residual NBDI | 0.61 | | | 0.25 | |
| Viscosity in mPa · s at 25° C. and at 100% solids content | solid* | solid** | 140 | 4100 | 4500 |
| Hazen colour | 10-15 | 10-15 | 10-15 | 10-15 | 10-15 |
| % of primary HDI n-butyl allophanate | | | 56.8% | 34 | 34 |
| % true (cyclo)tri-condensate | 74% | 70% | 0% | 29.6 | 28 |
| G ratio true (cyclo)tri-condensate/ sum of the (cyclo)tri-condensates | 0.74 | 0.7 | 0 | 0.74 | 0.7 |
| Primary allophanate/ primary allophanate + true (cyclo)tri-condensate | | | | 53.5 | 55 |
| Increase in viscosity | | | | >50% | >50% |

*4070 mPa · s at 25° C. and at 80% solids content in n-butyl acetate
**13400 mPa · s at 25° C. and at 80% solids content in n-butyl acetate.

The increases in viscosity are significantly greater than 50% given the fact that the products are solid and that the viscosity measured at 80% solids content is equivalent to or even greater than the viscosity of the two compositions.

EXAMPLE 10

Preparation of NBDT/HDT and Low-Viscosity HDI N-Butyl Allophanate Compositions The compositions were prepared as indicated in the following table:

| | Product of Example 8 | Product of Example 1 | Product of Example 2 | Characteristics of the mixtures |
|---|---|---|---|---|
| % of composition by weight | | | | 45/15/40 Pdt1/Pdt2/Pdt8 |
| DC of HDI | | 19.3 | 50% | |
| DC of NBDI | 20% | | | |
| Residual HDI | | 0.15 | 0.05 | 0.07 |
| Residual NBDI | 0.61 | | | 0.25 |
| Viscosity in mPa · s at 25° C. and at 100% solids content | Solid* | 1260 | 140 | 18500 |
| Hazen colour | 10-15 | 5 | 10-15 | 10-15 |
| % of primary HDI n-butyl allophanate | | 0.7 | 56.8% | 8.7 |
| % true (cyclo)tri-condensate | 74% | 61 | 0% | 57 |
| G ratio true (cyclo)tri-condensate/sum of the (cyclo)tri-condensates | 0.74 | 0.69 | 0 | 0.72 |
| Primary allophanate/ primary allophanate + true (cyclo)tri-condensate | | | | 13 |
| Biuret | | 6% | | 2.5% |
| Increase in viscosity | | | | 34% |

*4070 mPa · s at 25° C. and at 80% solids content in n-butyl acetate
**13400 mPa · s at 25° C. and at 80% solids content in n-butyl acetate.

The mixtures of the products of Examples 8 and 1 in a 52/48 ratio by weight has a viscosity of about 2800 mpa·s at 25° C. and at 100% solids content.

The increases in viscosity are significantly greater than 50% given the fact that the products are solids and that the viscosity measured at 80% solids content is equivalent to or even greater than the viscosity of the two compositions.

The invention claimed is:

1. A process for preparing a tricondensate polyfunctional isocyanate composition, comprising:
    A) the following step a) and b) in any order:
        a) (cyclo)condensing one or more identical or different first isocyanate monomer(s) to obtain a tricondensate polyfunctional isocyanate reaction product;
        b) reacting one or more second isocyanate monomer(s) which are identical to or different from one another and identical to or different from the first isocyanate monomer(s), the second monomer(s) being linear alkyl isocyanate monomer(s), with $C_4$-$C_8$ linear alkyl alcohol(s) to obtain an allophanate of one or more identical or different isocyanates, or a mixture of different allophanates;
    B) step c) and d) in any order:
        c) adding the reaction product from step b) to the reaction product from step
        a), and optionally,
        d) removing the isocyanate monomer(s), and
    C) obtaining a low-viscosity tricondensate polyfunctional isocyanate composition, wherein said composition comprises less than 2% of tricondensate allophanate relative to the total weight of the composition.

2. A process for preparing a low viscosity tricondensate polyfunctional isocyanate composition, comprising at least one isocyanurate and/or biuret group, which comprises the steps of: (1) preparing a tricondensate polyfunctional isocyanate reaction product, or a mixture of different tricondensate polyfunctional isocyanates reaction products, by (cyclo)trimerization of one or more identical or different isocyanate monomers and optionally of another monomer, (2) preparing an allophanate of one or more identical or different linear alkyl isocyanates, or a mixture of different allophanates by reacting a $C_4$-$C_8$ linear alkyl alcohol with said one or more identical or different linear alkyl isocyanates, and (3) admixing said tricondensate polyfunctional isocyanate reaction product or said mixture of different tricondensate polyfunctional isocyanate reaction products prepared from step (1) above with allophanate or mixture of different allophanates prepared in step (2) above, the isocyanates or mixtures of isocyanate monomers used to prepare the polyfunctional isocyanate(s) reaction product(s) being identical to or different from the isocyanate(s) or the mixture of isocyanates used to prepare the allophanate(s), wherein said composition comprises less than 2% of tricondensate allophanates relative to the total weight of the composition.

3. The process of claim 1 or claim 2, wherein the tricondensate polyfunctional isocyanate reaction product has the following general formula:

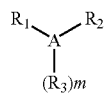

(I)

in which A represents:

an isocyanurate group of formula:

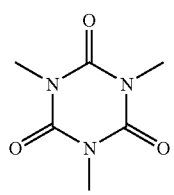

an imino-oxadiazine-dione of the following formula:

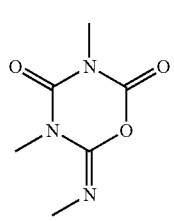

an oxadiazine-trione of the following formula:

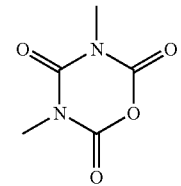

a biuret group of formula

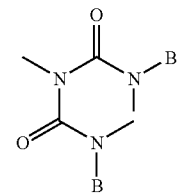

B being H or a $C_{1-20}$ group containing optionally, other atoms; or a group of formula:

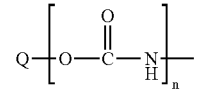

and in which $R_1$, $R_2$ and $R_3$, identical or different, represent a group containing carbon and hydrogen, comprising a true isocyanate function or a derived function selected from the group consisting of carbamate, urea, biuret, urethane, uretinedione, isocyanurate and masked isocyanate, wherein at least one of $R_1$, $R_2$ and $R_3$, comprises a true isocyanate function or a derived isocyanate function, said derived isocyanate function being a masked isocyanate;

Q is a group, as defined for $R_1$ to $R_3$, m is an integer from 0 to 2, and n is the integer 3 or 4.

4. The process of claim 1 or 2, wherein the low viscosity tricondensate polyfunctional isocyanate composition comprises at least one isocyanurate polyisocyanate.

5. The process of claim 1 or claim 2, wherein the allophanates are of the following formula II:

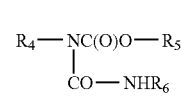

(II)

in which:

$R_4$ and $R_6$, identical or different, represent a group containing carbon and hydrogen comprising a true isocyanate function or a derived function selected from the group consisting of carbamate, urea, biuret, urethane, uretinedione, masked isocyanate and allophanate, $R_5$ represents a $C_4$-$C_8$ linear alkyl group.

6. The process of claim 1 or claim 2, wherein a mixture of allophanates is added to the tricondensate polyfunctional isocyanate reaction product(s).

7. The process of claim 1 or claim 2, wherein the mixture of allophanates comprises mono-, bis- and trisallophanates, in an amount of at least ⅔, by weight relative to the total weight of the allophanate mixture after removal of unreacted monomers.

8. The process of claim 1 or claim 2, wherein the mixture of allophanates comprises mono-, bis- and trisallophanates, in an amount of at least 75%, by weight relative to the total weight of the allophanate mixture after removal of unreacted monomers.

9. The process of claim 1 or claim 2, wherein the mixture of allophanates comprises mono-, bis- and tris-allophanates, in an amount of at least 90%, by weight relative to the total weight of the allophanate mixture after removal of unreacted monomers.

10. The process of claim 1 or claim 2, wherein the bis-allophanate represented up to 10% of the total weight of the allophanate.

11. The process according to claim 1 or claim 2, wherein tris-allophanates are less than or equal to 30%, relative to the total weight of the allophanate.

12. The process according to claim 1 or claim 2, wherein tris-allophanates are less than or equal to 20%, relative to the total weight of the allophanate.

13. The process according to claim 1 or claim 2, wherein tris-allophanates are less than or equal to 15%, relative to the total weight of the allophanates.

14. The process of claim 1 or claim 2, wherein the mixture of allophanates comprises mono-, bis- and tris-allophanates and the ratio bis-allophanate functions+tris-allophanate functions/mono-allophanate functions is equal to or greater than 0.1.

15. The process of claim 1 or claim 2, wherein the mixture of allophanates comprises mono-, bis- and tris-allophanates and the ratio bis-allophanate functions+tris-allophanate functions/mono-allophanate functions is equal to or greater than 0.3.

16. The process of claim 1 or claim 2, wherein the mixture of allophanates comprises mono-, bis- and tris-allophanates and the ratio bis-allophanate functions+tris-allophanate functions/mono-allophanate functions is equal to or greater than 0.5.

17. A process for preparing a low-viscosity tricondensate polyfunctional isocyanate composition, comprising the following steps a) and b) in any order:
  a) (cyclo)condensating, in the presence of a catalyst, of one or more identical or different first isocyanate monomer(s) until a degree of conversion is obtained;
  b) reacting one or more second isocyanate monomer(s) which are identical to or different from one another and identical to or different from the first isocyanate monomer(s), with a $C_4$-$C_8$ linear alkyl alcohol to form a carbamate, the reaction optionally being catalyzed, and simultaneous or subsequent reaction of the carbamate with one or more isocyanate monomer(s) which are identical to or different from the previous monomers, to give an allophanate or mixture of allophanates;
and steps c) and d) in any order:
  c) mixing the reaction product from step a) with all or some of the reaction product from step b) and optionally
  d) removing the isocyanate monomers, wherein said composition comprises less than 2% of tricondensate allophanates relative to the total weight of the composition.

18. The process of claims 1 or 17, wherein the isocyanate(s) used for the (cyclo)condensation reaction is (are) identical to the isocyanate(s) used for the allophanatization reaction.

19. The process of claims 1 or 17, wherein the isocyanate(s) used for the allophanatization reaction and the isocyanate(s) used for the cyclocondensation reaction satisfy one, two or three of the following conditions:
  at least one or at least two of the NCO functions are linked to a carbon-containing skeleton via a saturated ($sp^3$) carbon;
  at least one or at least two of said saturated ($sp^3$) carbons bears at least one hydrogen(s)
  all the intermediate carbons via which the isocyanate functions are linked to the carbon-containing skeleton are saturated ($sp^3$) carbons which partially, or totally, bear one hydrogen or two hydrogens.

20. The process of claim 17, wherein the NCO/OH ratio of the isocyanate and the alcohol in step b) is greater than 4.

21. A low viscosity tricondensate polyfunctional isocyanate composition comprising at least one true tricondensate polyfunctional isocyanate and at least one primary allophanate prepared from a $C_4$-$C_8$ linear alkyl alcohol, said composition comprising less than 2% of tricondensate allophanates relative to the total weight of the composition.

22. A low viscosity tricondensate polyfunctional isocyanate composition comprising at least one true tricondensate polyfunctional isocyanate and at least one primary allophanate prepared from a $C_4$-$C_8$ linear alkyl alcohol, said composition comprising less than 1% of tricondensate allophanates relative to the total weight of the composition.

23. The low viscosity tricondensate polyfunctional isocyanate composition of claim 21, said composition satisfying at least one of the following conditions:
  a G ratio defined by:

$$G = \frac{\text{true tricondensate polyisocyanates, obtained from the condensation of three identical or different isocyanate molecules not modified with carbamate or allophanate}}{\text{sum of the polyisocyanate molecules bearing at least one tricondensate function obtained from the condensation of three identical or different isocyanate molecules}}$$

where G is greater than 0.3,
  an allophanate/allophanate+true trimer weight ratio of between 2.5% and 99%,
  the tricondensates are obtained from a tricondensation reaction for which the degree of conversion of the identical or different isocyanate monomer(s) into tricondensate polyfunctional polyisocyanate reaction products contained in the composition is greater than 8%,
  at least 1% and not more than 99%, of biuret is present, these amounts being given on a weight basis.

24. The low viscosity tricondensate polyfunctional isocyanate composition of claims 21 or 23, wherein the allophanates comprises mono-, bis- and tris-allophanates in an amount of at least ⅔, by weight relative to the total weight of the allophanate after removal of unreacted monomers.

25. The low viscosity tricondensate polyfunctional isocyanate composition of claims 21 or 23, comprising an amount of bis-allophanate representing up to 10%, of the total weight of the allophanate.

26. The low viscosity tricondensate polyfunctional isocyanate composition of claims 21 or 23, comprising an amount of tris-allophanates less than or equal to 30%, by weight relative to the total weight of the composition.

27. The low viscosity tricondensate polyfunctional isocyanate composition of claims 21 or 23, comprising a ratio bis-allophanate functions+tris-allophanate functions/monoallophanate functions greater than or equal to 0.1, and up to 0.3.

28. The low viscosity tricondensate polyfunctional isocyanate composition of claim 21, comprising hexamethylene diisocyanate biuret.

* * * * *